United States Patent [19]

Anderson

[11] Plant 4,319

[45] Oct. 17, 1978

[54] ALMOND TREE (17-J-495)

[75] Inventor: Frederic W. Anderson, Merced, Calif.

[73] Assignee: The Burchell Nursery, Inc., Modesto, Calif.

[21] Appl. No.: 873,290

[22] Filed: Jan. 30, 1978

[51] Int. Cl.[2] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is very large, open to dense, vigorous, stocky to medium in trunk form, spreading to medium in branching habit, foliated with medium size, ovate leaves having a crenate margin and globose glands, blooms medium to late with white flowers, and, with medium productivity, is an irregular bearer of late harvesting, medium-to-small size, oval-to-ovate nuts having an oval-to-ovate kernel; the tree being particularly characterized by having red anthers on the stamens of its flowers, and by being self-fruitful.

1 Drawing Figure

BACKGROUND OF THE VARIETY

1. Field of the Discovery

Over a substantial number of years I have engaged in an extensive and continuing plant breeding program at my experimental nursery and orchard located near Le Grand, Merced County, Calif.; one purpose of such program being to provide improved varieties of nut trees. The present variety of almond tree resulted from my endeavors in the conduct of such plant breeding program; such variety being embraced by Class 30, Plants, of the U.S. Patent Office Manual of Classification.

2. Prior Varieties

Among the existent varieties of almond trees which are known to me are those mentioned herein for the purpose of comparison; to-wit, Mission (unpatented), Ruby (U.S. Plant Pat. No. 1,698), and Ripon (U.S. Plant Pat. No. 2,379).

ORIGIN OF THE VARIETY

The present variety of almond tree was originated by me in my experimental nursery and orchard, located as aforesaid, as a cross between the Ripon and an unnamed self-fruitful almond seedling. Such cross was maintained by me under careful and continuing observation and when—in maturity—it evidenced novel and desirable characteristics for commercial production, asexual reproduction was undertaken by me.

ASEXUAL REPRODUCTION OF THE VARIETY

Subsequent to my origination of the present variety of almond tree, I asexually reproduced it by top-working on mature trees in my said experimental orchard, and—in maturity—such reproductions ran true to the original tree in all respects.

SUMMARY OF THE VARIETY

The herein-claimed new and distinct variety of almond tree is very large, open to dense, vigorous, stocky to medium in trunk form, spreading to medium in branching habit, foliated with medium size, ovate leaves having a crenate margin and globose glands, blooms medium to late with white flowers, and, with medium productivity, is an irregular bearer of late harvesting, medium-to-small size, oval-to-ovate nuts having an oval-to-ovate kernel.

The variety is further, and more particularly, characterized by flowers having red anthers on the stamens, and by being self-fruitful. In these two characteristics, the present variety resembles peaches and nectarines, and in contrast all commercial almond varieties have yellow anthers on the stamens, and are self-unfruitful.

BRIEF DESCRIPTION OF THE DRAWING

The drawing is an illustration, by photographic reproduction in color, of twigs with leaves, nuts in hull, nuts out of hull, and shelled kernels.

DESCRIPTION OF THE VARIETY

The botanical details of this new and distinct variety of almond tree—with color definitions in common color terms—are as follows:

Tree:
- *Density.*—Open to dense.
- *Size.*—Very large.
- *Vigor.*—Vigorous.

Trunk:
- *Form.*—Stocky to medium.

Branches:
- *Form.*—Medium.
- *Branching habit.*—Spreading to medium.
- *Color.*—New wood — brown to gray. Mature wood — brown to gray.

Foliage:
- *Quantity.*—Medium.

Leaves:
- *Size.*—Medium. Average length — $3\frac{1}{4}''$. Average width — $1\frac{1}{8}''$.
- *Shape.*—Ovate.
- *Thickness.*—Medium.
- *Margin.*—Crenate.
- *Petiole.*—Medium length. Medium thickness.
- *Glands.*—Globose. Usually positioned 2 on petiole and 1 or 2 on blade.
- *Color.*—Top side — Medium green. Under side — Lighter green.

Bloom:
- *Amount of bloom.*—Average.
- *Color.*—White.

*Blooming period.*—Medium to late — about with Ruby.

Crop:

*Bearing.*—Irregular bearer.

*Productivity.*—Medium.

*Distribution of nuts on tree.*—Well distributed.

*Harvest period.*—Sept. 25, 1977. Late, as compared to Mission.

*Tenacity.*—Tendency to drop off early. Easy to harvest. Easy to hull and shell.

Hull:

*Outer surface.*—Smooth.

*Form.*—Regular.

*Thickness.*—Thin.

*Flesh.*—Fleshy to tough.

*Suture.*—Flat.

*Color.*—Light green.

*Dehiscence.*—Opens partially.

*Splitting.*—Along suture. Freely at base.

Nut:

*Size.*—Medium to small. Average length — $1\frac{1}{4}''$. Average width — $\frac{7}{8}''$. Average thickness — $\frac{5}{8}''$. Average weight — 14 per ounce.

*Form.*—Length/width — Oval to ovate. Width/-Thickness — Medium.

*Shell.*—Hard. Thick. Smooth. Outer shell — hard. Inner shell — hard. Well sealed.

*Color.*—Beige.

*Pits.*—Small. Numerous. Shallow. Irregular.

*Base.*—Square.

*Stem scar.*—Small.

*Apex.*—Acute. Tip recurved.

*Wing.*—Narrow. Thin.

*Inner surface.*—Light colored.

*Percentage of kernel to nut.* —45%.

Kernel:

*Size.*—Medium. Average length — $\frac{3}{4}''$. Average width — $\frac{1}{2}''$. Average thickness — 5/16th ". Average weight — 33 per ounce.

*Form.*—Length/width — Oval to ovate. Width/-thickness — medium.

*Base.*—Square.

*Stem scar.*—Large to small. Obtuse.

*Apex.*—Obtuse to acute.

*Texture.*—Wrinkled.

*Pellicle.*—Thick to thin.

*Color.*—Medium light brown.

*Number of Doubles.*—None to few.

*Defective kernels.*—Very few.

*Flavor.*—Normal.

*Quality.*—Good.

Resistance to insects and diseases: No unusual susceptibilities noted.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by flowers having red anthers on the stamens, and by being self-fruitful.

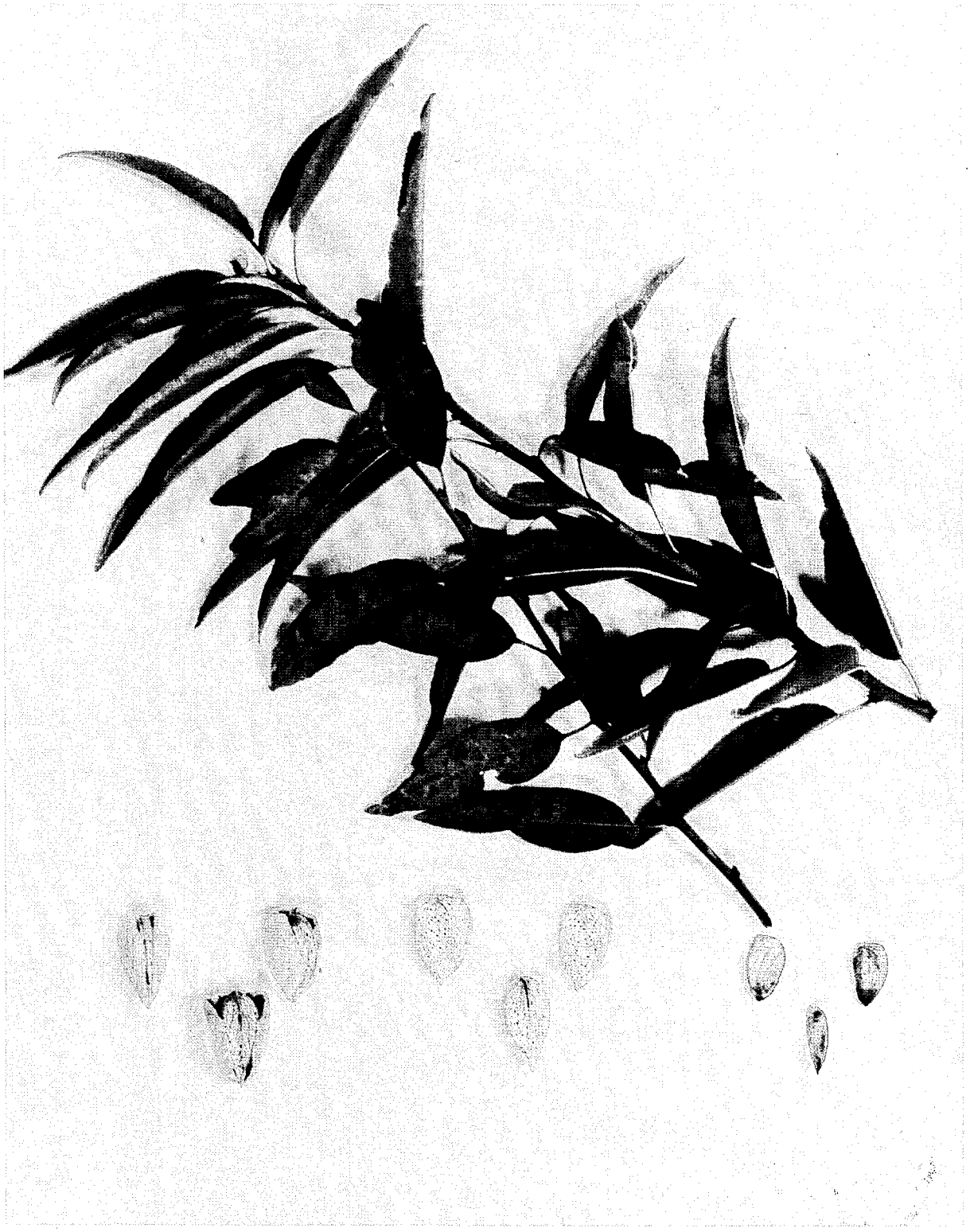

* * * * *